(12) United States Patent
Scullin et al.

(10) Patent No.: US 11,807,983 B2
(45) Date of Patent: Nov. 7, 2023

(54) PENETRATION AND ADHESION OF FINISHES FOR FUNGAL MATERIALS THROUGH SOLUBILIZATION, EMULSION, OR DISPERSION IN WATER-SOLUBLE MATERIALS AND THE USE OF SURFACTANTS

(71) Applicant: Mycoworks, Inc., Emeryville, CA (US)

(72) Inventors: Matt Scullin, San Francisco, CA (US); Nicholas Wenner, Sebastopol, CA (US); Jordan Chase, Oakland, CA (US); Quinn Miller, Berkeley, CA (US); Philip Ross, Sam Francisco, CA (US)

(73) Assignee: MycoWorks, Inc., Emeryville, CA (US)

(*) Notice: Subject to any disclaimer, the term of this patent is extended or adjusted under 35 U.S.C. 154(b) by 0 days.

(21) Appl. No.: 16/664,662

(22) Filed: Oct. 25, 2019

(65) Prior Publication Data
US 2020/0131694 A1    Apr. 30, 2020

Related U.S. Application Data

(60) Provisional application No. 62/750,358, filed on Oct. 25, 2018.

(51) Int. Cl.
*D06N 3/00*    (2006.01)
*C08G 63/08*    (2006.01)
(Continued)

(52) U.S. Cl.
CPC .......... *D06N 3/0002* (2013.01); *C08G 63/08* (2013.01); *C09D 167/04* (2013.01);
(Continued)

(58) Field of Classification Search
CPC ............................. C08G 63/08; C09D 167/04
See application file for complete search history.

(56) References Cited

U.S. PATENT DOCUMENTS 2,917,410 A    12/1959   Vitalis
4,172,064 A    10/1979   Keller
(Continued)

FOREIGN PATENT DOCUMENTS

AU    20152711910 A1    7/2017
CA    2057669        *  6/1993
(Continued)

OTHER PUBLICATIONS

Copenheaver, Blaine R.; International Search Report from International Searching Authority with respect to PCT/US2019/058203; ISA/US; Jan. 15, 2020.
(Continued)

*Primary Examiner* — Tae H Yoon
(74) *Attorney, Agent, or Firm* — Temmerman Law; Mathew J. Temmerman

(57) ABSTRACT

An abrasion resistant finish for a fungal material, the finishing comprising an optimum quantity biodegradable polylactic acid plastic (PLA) dispersed in water to produce a PLA mixture. When the PLA mixture is applied to the fungal material, water carries the PLA deeply into the matrix of the fungal hyphae to a depth at least 2 N/10 mm or 1% of the thickness of the fungal material, whichever is greater. The finish fortifies the hyphal structure as the water evaporates and creates a PLA coating on the fungal material with improved abrasion resistance and water resistance.

6 Claims, 3 Drawing Sheets

(51) Int. Cl.
*D06N 3/12* (2006.01)
*D06N 3/14* (2006.01)
*C09D 167/04* (2006.01)
*D06N 3/18* (2006.01)

(52) U.S. Cl.
CPC .......... *D06N 3/0056* (2013.01); *D06N 3/123* (2013.01); *D06N 3/143* (2013.01); *D06N 3/183* (2013.01)

(56) References Cited

U.S. PATENT DOCUMENTS

| | | | |
|---|---|---|---|
| 4,803,800 A | 2/1989 | Romaine et al. | |
| 8,258,254 B2 | 9/2012 | Inoue et al. | |
| 8,298,809 B2 | 10/2012 | Kalisz et al. | |
| 9,072,334 B2 | 7/2015 | Schaefer | |
| 9,555,395 B2 | 1/2017 | Araldi et al. | |
| 2015/0337094 A1 | 11/2015 | Wong et al. | |
| 2017/0095760 A1* | 4/2017 | Stonecipher | B60H 3/0608 |
| 2017/0367964 A1* | 12/2017 | Yamamoto | A61K 8/81 |
| 2018/0146627 A1 | 5/2018 | Ross et al. | |
| 2018/0148682 A1 | 5/2018 | Ross | |
| 2018/0282529 A1* | 10/2018 | Kaplan-Bie | D06N 3/00 |
| 2020/0131694 A1* | 4/2020 | Scullin | D06N 3/123 |
| 2021/0332243 A1* | 10/2021 | Forgacs | B32B 7/12 |
| 2021/0401112 A1* | 12/2021 | Smith | C07K 14/43563 |

FOREIGN PATENT DOCUMENTS

| | | | |
|---|---|---|---|
| JP | 2001501652 A | * | 2/2001 |
| WO | 2018183735 A1 | | 10/2018 |

OTHER PUBLICATIONS

Lelivelt, R.J.J., The mechanical possibilities of mycelium materials, Journal, Eindhoven University of Technology, Mar. 2, 2015.
European Patent Office, search report for EU Patent App 19876048.0, dated Jul. 18, 2022.
Extended European Patent Office, search report for EU Patent App 19876048.0, dated Dec. 13, 2022.

* cited by examiner

PENETRATION AND ADHESION OF FINISHES FOR FUNGAL MATERIALS THROUGH SOLUBILIZATION, EMULSION, OR DISPERSION IN WATER-SOLUBLE MATERIALS AND THE USE OF SURFACTANTS

RELATED APPLICATIONS

This application claims the benefit of U.S. provisional patent application 62/750,358, filed Oct. 25, 2018, the disclosure of which is incorporated herein in its entirety.

BACKGROUND OF THE DISCLOSURE

Technical Field of the Disclosure

This invention relates generally to finishes applied to fungal materials, and more specifically to a finish with improved adhesion and penetration into a fungal material.

Description of the Related Art

Fungal materials have emerged as versatile biomaterials with a variety of mechanical and physical uses. One such manifestation of fungal material is as a textile, i.e., in thin sheets used in the fabrication of finished goods such as shoes, bags, and clothing, and in any use case where a flexible fabric is utilized. In order for fungal materials to be useful in these applications, they must be processed so as to embody suitable mechanical properties including but not limited to those of tensile strength, tear strength, stitchability, abrasion resistance, colorfastness, dye transfer, flexing endurance, ply adhesion, surface adhesion, and finish adhesion.

A typical mechanical property profile for soft, flexible, fabric-like materials, such as leather and other textiles, can exhibit high strength and tear resistance; but due to the very softness that makes said material desirable as a textile, can also perform poorly under abrasion. This is to say, that even through a textile may endure high tensile strength, the surface layer of this material may abrade away under friction, and furthermore, if dyed, the material may transfer color to other objects it rubs against throughout daily use: such as a handbag that rubs against the blouse of the person wearing them.

Fungal materials are highly water-absorbent, with natural water content routinely above 85% when alive or growing. The sponge-like nature of the material contributes to this; whereby the interstitial spaces between individual hyphae, the material making up those hyphae, and generally in the void space throughout a mycelium; absorb large amounts of water. When coating materials are dissolved, emulsified, or dispersed in water; or when such coating materials are packaged in a micelle and dispersed in a colloidal solution; and subsequently applied to fungal materials; the water is absorbed deeply into both the micro and macrostructure of the fungal material, carrying the coating materials along with it.

Water-based finishes for fungal materials provide both environmental and performance advantages unavailable through other methods. For example, they can replace finishes based on toxic solvents while producing finishes with higher penetration and greater adhesion. Similarly, mycelium is naturally resistant to penetration by high-molecular weight materials such as large-molecule lubricants and oils, but mycelium is very hydrophilic, and thereby absorbs water based solutions, emulsions, and dispersions. Furthermore, the use of surfactants can also overcome the tendency to adsorb instead of absorb materials, whereby the molecule that is needed for to penetrate is enclosed in a package of distinct pH (thus cationic or anionic charge), so that ionic forces can be used to facilitate absorption of coating materials and other chemicals.

Conventional methods of applying finishes on fungal materials include applying biodegradable polymers, such as the polyester poly(L-lactic acid) (hereinafter "PLA") or other polyhydroxyacids with on heat and pressure or via toxic solvents. For example, thin films of PLA may be laminated onto fungal materials using heat and pressure with machines like roll laminators. Further, PLA or other biodegradable polymers may also be applied by dissolving it in a chlorinated organic solvent such as methylene chloride and applying the solution to the surface with a brush or spray. When the solvent evaporates, a layer of PLA or other biodegradable polymers remains, coating the material. However, neither method produces a strongly adhered or deeply penetrated layer; which is to say the coating is merely adsorbed—resulting in a separate layer of molecules without interpenetration of mycelium and coating. Moreover, the solvent method creates significant environmental and workplace safety challenges.

There is thus a need for an improved abrasion resistant finish for a fungal material and a method for creating the abrasion resistant finish. Such an abrasion resistant finish would provide improved adhesion and penetration into the fungal material. Such a finish would not use any toxic chemicals and not cause harmful side effects. Further, such a finish would improve abrasion resistance, colorfastness to crocking, dye transfer and water resistance of the fungal material. Moreover, such an improved abrasion resistant finish would not require specific conditions like heat, pressure or any toxic solvents to apply the finish onto the fungal material. Furthermore, such an abrasion resistance finish would not cause any environmental and workplace challenges. The present embodiment overcomes shortcomings in the field by accomplishing these critical objectives.

SUMMARY OF THE DISCLOSURE

To minimize the limitations found in the existing systems and methods, and to minimize other limitations that will be apparent upon the reading of this specification, a preferred embodiment of the present invention provides an abrasion resistant finish for a fungal material and a method for making and applying the abrasion resistant finish onto the fungal material.

The abrasion resistant finish of the preferred embodiment of the present invention comprises an optimum quantity biodegradable polymer dispersed in water to produce a mixture. In one embodiment the polymer is PLA, which will be used here for example purposes only. In this example, the concentration of the PLA dispersed in water ranges from 0.1%-50%. When the PLA mixture is applied to the fungal material, water carries the PLA deeply into the matrix of the fungal hyphae, fortifies the hyphal structure as the water evaporates and creates a coating on the fungal material with improved abrasion resistance and water resistance. Environmental concerns are greatly minimized by dispersing PLA in water.

The method for creating the abrasion resistant finish for the fungal material comprises the steps of: providing an optimum quantity of biodegradable polylactic acid (PLA), dispersing the optimum quantity biodegradable PLA into water to produce a PLA mixture and applying the PLA mixture onto the fungal material such that the water carries the PLA deeply into the fungal matrix. Next, the process allows the fungal material to dry such that the water evaporates thereby creating a PLA coating on the fungal material with improved abrasion and water resistance. Although many steps herein are described with respect to PLA, it is to be understood other biodegradable polymers may be substituted in its place.

A first objective of the present embodiment is to provide an improved abrasion resistant finish for a fungal material and a method for creating the abrasion resistant finish.

A second objective of the present embodiment is to provide an abrasion resistant finish that provides improved adhesion and penetration into the fungal material.

A third objective of the present embodiment is to provide an abrasion resistant finish that does not use any toxic chemicals and thus minimizes harmful side effects.

A fourth objective of the present embodiment is to provide a finish that provides improved abrasion resistance, colorfastness to crocking, reduced dye transfer, and water resistance of the fungal material.

A fifth objective of the present embodiment is to provide an improved abrasion resistant finish that does not require specific conditions like heat, pressure or any toxic solvents to apply the finish onto the fungal material.

Another objective of the present embodiment is to provide an abrasion resistance finish that minimizes or removes environmental and related workplace challenges.

These and other advantages and features of the present invention are described with specificity so as to make the present invention understandable to one of ordinary skill in the art.

BRIEF DESCRIPTION OF THE DRAWINGS

In order to enhance their clarity and improve the understanding of the various elements and embodiments, the figures have not necessarily been drawn to scale. Furthermore, elements that are known to be common and well understood to those in the industry are not necessarily depicted, thus providing a clear view of the various embodiments of the invention. Thus, the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term 'about" means+/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application. Finally, although many examples herein describe the biodegradable polymer PLA, the methods and compositions may equally include other polyhydroxyacids, or for that matter any polyester or any biodegradable polymer.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

The present invention pertains to water-based finishes for fungal materials for improving abrasion resistance, colorfastness to crocking, dye transfer, water resistance, and other attributes. The advantages conferred by water-based finishes come in part from greater penetration and adhesion of the finishes compared to conventional methods.

Figure 1A:
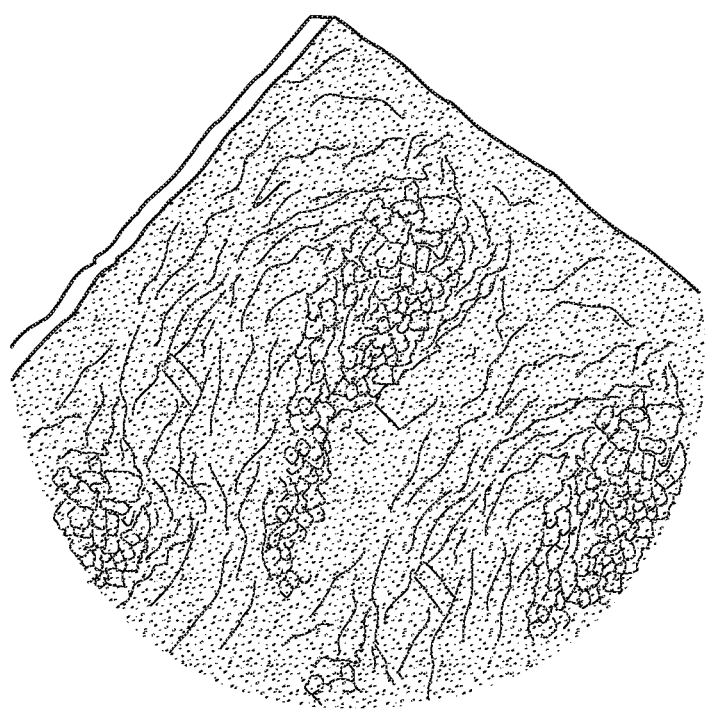
FIG. 1A illustrates a prior art image of a water insoluble PLA coating applied to a fungal material.
Figure 1B:
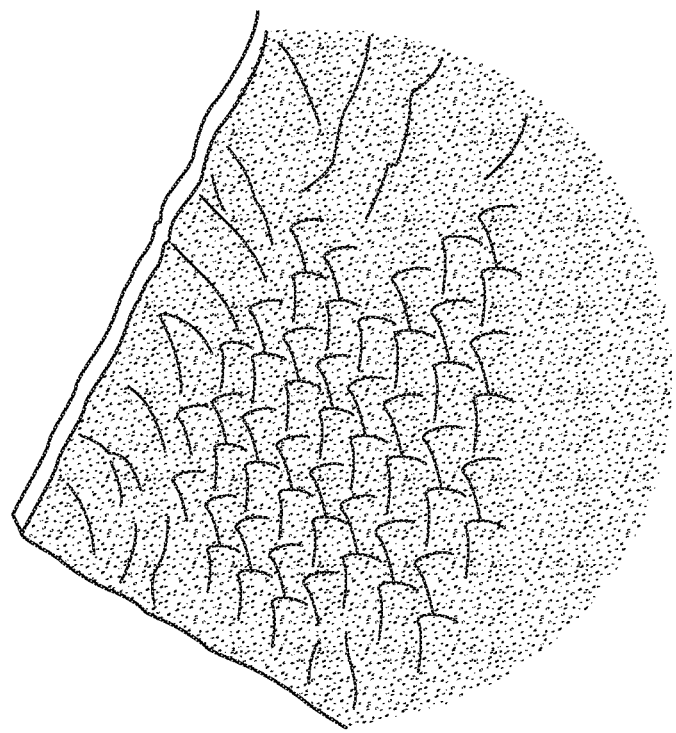
FIG. 1B illustrates a prior art image of the water insoluble PLA coating applied to another fungal material.

Referring to FIGS. 1A and 1B, prior art images of a fungal material coated with a water insoluble PLA coating are illustrated. It is to be understood that other biodegradable polymers may be substituted. PLA is applied to the fungal material via a water insoluble chlorinated solvent. The resulting layer of PLA has both low penetration and low adhesion, resulting in delamination between the PLA and the fungal substrate upon bending as illustrated in FIGS. 1A and 1B.

Figure 2B:
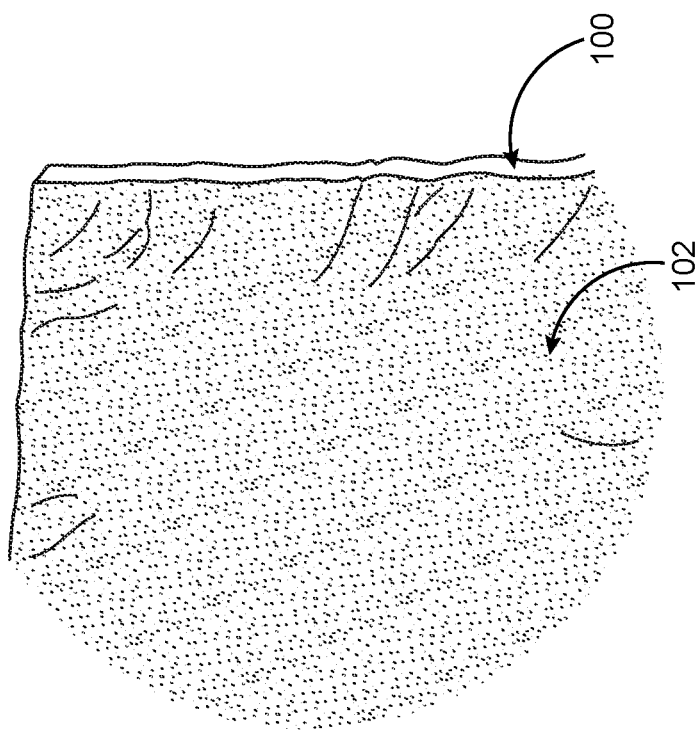
FIG. 2B illustrates an image of the abrasion resistant finish applied to another fungal material in accordance with the preferred embodiment of the present invention.
Figure 2A:
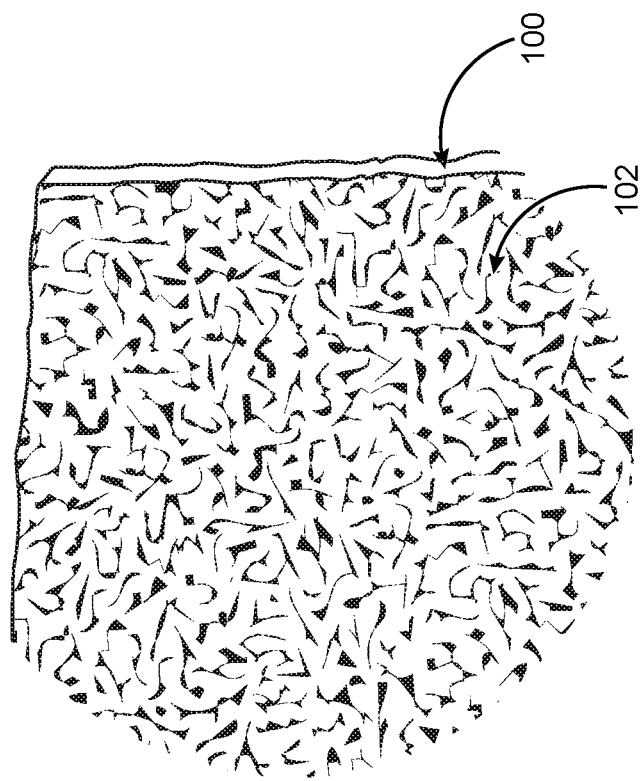
FIG. 2A illustrates an image of an abrasion resistant finish applied to a fungal material in accordance with the preferred embodiment of the present invention.
Figure 3:
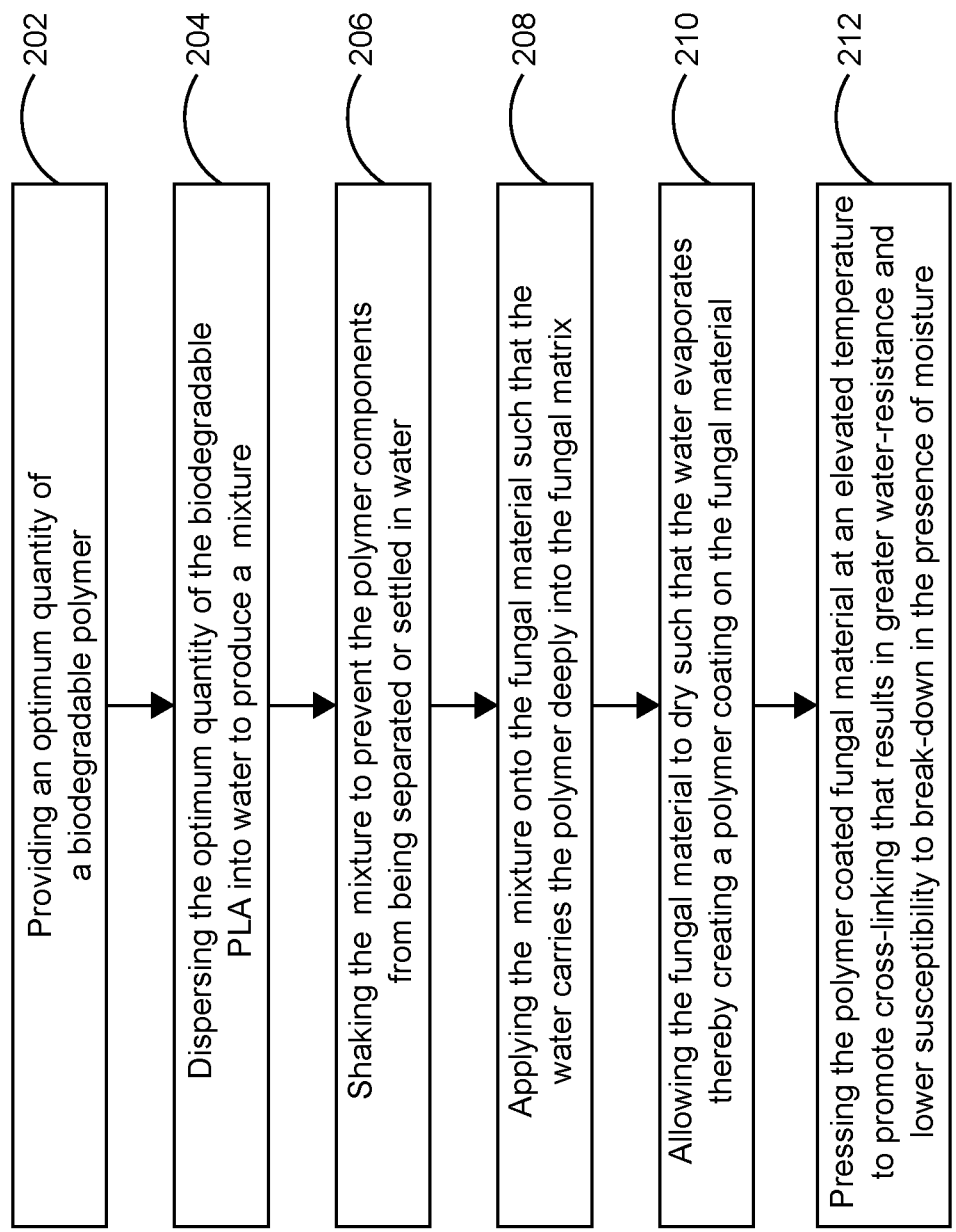
FIG. 3 illustrates a flowchart of a method for producing and applying the abrasion resistant coating on the fungal material in accordance with the preferred embodiment of the present invention.

FIGS. 2A-2B illustrates images of an abrasion resistant finish 102 applied to a fungal material 100 in accordance with the preferred embodiment of the present invention. The preferred embodiment provides an abrasion resistant finish 102 having high penetration and high adhesion when applied onto the fungal material 100. The fungal material 100 is preferably mycelium. The abrasion resistant finish 102 comprises an optimum quantity biodegradable polymer is dispersed in water to produce a mixture. The biodegradable polymer is a polyester. The polyester utilized as the biodegradable polymer is polylactic acid (PLA). The polylactic acid (PLA) is dispersed in water to produce a PLA mixture. The optimum quantity of the biodegradable PLA depends on the thickness of the PLA coating to be applied on the fungal material 100 and the surface density of the fungal material 100. The concentration of the PLA dispersed in water may range from 0.1%-50%. Additional moisture may also be included in the PLA dispersion in order to promote penetration into the surface of the fungal material 100 depending on the moisture content of the PLA to which is being applied.

When PLA is dispersed in water to produce the PLA mixture, environmental concerns are greatly minimized. When applied to the fungal material 100, water carries the PLA more deeply into the micro and macro structure of the hydrophilic fungal material 100. PLA is carried to a depth of at least 20 micrometers, or at least 1% of the thickness of the fungal material 100, whichever is smaller. In embodiments where the material thickness is from at least 0.5 to 5 mm, the depth of at least 1% yields a penetration of from at least 5 microns and 50 microns. The PLA penetrates deeply into the fungal material 100, fortifies the hyphal structure and creates a biodegradable PLA coating adhered on top of the fungal material 100 with improved abrasion resistance and water resistance. When PLA is applied to fungal material 100 via dispersion in water, the resulting layer of PLA coating has both high penetration and high adhesion, resulting in strong cohesion between the PLA coating and the fungal material 100 under bending, as illustrated in FIGS. 2A and 2B. The resultant fungal material has a penetration of its finish to a depth of at least 1% of the thickness of the material or 20 micrometers, whichever is smaller, and has a finish adhesion of >2 N/10 mm according to ISO 11644:2009.

In another embodiment of the present invention, the PLA coating includes polyurethane, acrylic, resin or silicone and is applied to the fungal material 100 to achieve improved abrasion resistance, water resistance, color transfer, light-fastness, hand feel and color. Such PLA coating may be applied using water-soluble solvents and surfactants that include isopropyl alcohol, glycols or glycerols, or a solubility enhancer. These coatings are applied in multiple steps via spray or roll-transfer so as to achieve the desired combination of properties, such as a polyurethane or acrylic containing layer to promote adhesion followed by additional layers that contain color pigment, other acrylics, silicones, resins or polyurethanes or the like, and dried in between the application of layers and heated and pressed such as through a heated roller after application. Thus, the PLA coating produces a structure whereby a polyurethane, acrylic, resin, or silicone rich layer is adhered to the surface of the fungal material 100 with adhesion strength of greater than 2 Newtons per 10 mm according to ISO 11644:2009.

In one embodiment of the present invention, at least one surfactant is added to the abrasion resistant finish 102 to improve the effectiveness of the abrasion resistant finish 102. The at least one surfactant is added to the water-based adhesion PLA coating in a three-part leather spray coating process to improve the effectiveness of the adhesion PLA coating. In a preferred embodiment, 200-800 parts water, 200-400 parts polyurethane binder, 200-800 parts isopropyl alcohol, and 10-150 parts of 2-butoxyethanol are mixed and sprayed onto the fungal material 100. The addition of the surfactant serves to lower the surface tension of the PLA coating, improves the wetting of the fungal surface and draws the water-based finish 102 deeper into the fungal material 100.

In this embodiment, the addition of the surfactant lowers the surface tension of the finish 102 and further improves penetration. The PLA coating provides adhesion to the underlying fungal material 100, then a color pigment that gives color coat, and a top coat gives abrasion resistance and other desirable qualities. Adding the surfactant to the water-based PLA basecoat lowers surface tension and improves penetration and adhesion of the other two layers.

Surfactants are usually organic compounds that are amphiphilic, with both hydrophobic groups and hydrophilic groups. With both a water-insoluble component and a water-soluble component, surfactants will diffuse in water and adsorb at interfaces. The water-insoluble hydrophobic group extends out of the bulk water phase into the air while the water-soluble head group remains in the water phase.

Wetting is the ability of a liquid to maintain contact with a solid surface, resulting from intermolecular interactions when the two are brought together. The degree of wetting (wettability) is determined by a force balance between adhesive and cohesive forces. Adhesive forces between a liquid and solid cause a liquid drop to spread across the surface. Cohesive forces within the liquid cause the drop to ball up and avoid contact with the surface. Surfactants can be used to modify the adhesive and cohesive force balance to promote wetting.

The contact angle ($\theta$) is the angle at which the liquid—vapor interface meets the solid-liquid interface. The contact angle is determined by the balance between adhesive and cohesive forces. As the tendency of a drop to spread out over a flat, solid surface increases, the contact angle decreases. Thus, the contact angle provides an inverse measure of wettability.

A contact angle less than 90° (low contact angle) usually indicates that wetting of the surface is very favorable, and the fluid will spread over a large area of the surface. Contact angles greater than 90° (high contact angle) generally mean that wetting of the surface is unfavorable, and the fluid will minimize contact with the surface and form a compact liquid droplet.

One model for understanding the wetting characteristics of surfactants is known as excess free energy. The excess free energy of a system is the useful work obtainable from an isothermal isobaric thermodynamic system. The excess free energy $\Phi$ of a liquid droplet deposited on a solid substrate is given as follows:

$$\Phi = \gamma S + PV + \pi R2(\gamma sl - \gamma sv) \quad \text{(Equation 1)}$$

where S is the area of the liquid-vapor interface; $P = P_a - P_l$ is the excess pressure inside the liquid, $P_a$ and $P_l$ are the ambient air pressure and pressure inside the liquid, respectively; R is droplet base radius; $\gamma$, $\gamma sl$ and $\gamma sv$ are the liquid-vapor, solid-liquid and solid-vapor interfacial tensions, respectively. The last term in the right hand side of Eq. (1) provides the difference between the energy of the surface covered by the liquid drop and the energy of the same solid surface without the droplet. Eq. (1) shows that the excess free energy decreases if (a) the liquid-vapor interfacial tension decreases; (b) the solid-liquid interfacial tension decreases; and (c) the solid-vapor interfacial tension increases.

In the presence of surfactants the following three transfer processes take place from the liquid onto all three interfaces: surfactant adsorption at both (i) the inner solid-liquid interface and (ii) the liquid-vapor interface, and (iii) transfer of surfactant molecules from the drop onto the solid-vapor interface in front of the drop on the bare substrate. The adsorption processes (i) and (ii) results in a decrease of corresponding interfacial tensions $\gamma sl$ and $\gamma$. The transfer of surfactant molecules onto the solid-vapor interface in front of the drop results in an increase of a local free energy. In net, the process leads to a decrease of the excess free energy of the system, resulting in a decrease of the contact angle and increased wetting. In this way, adhesion and penetration of the water-based abrasion resistant finish 102 for fungal materials 100 can be improved by adding surfactants which decrease the wetting angle and improve wetting in the fungal material 100.

FIG. 3 illustrates a flowchart of a method for creating an abrasion resistant finish for a fungal material. The method comprises the steps of: providing an optimum quantity of a biodegradable polylactic acid (PLA) as indicated at block 202. Dispersing the optimum quantity of the biodegradable PLA into water to produce a PLA mixture as indicated at block 204. Then shaking or agitating the PLA mixture to prevent the PLA components from being separated or settled in water as indicated at block 206. Applying the PLA mixture onto the fungal material such that the water carries the PLA deeply into the fungal matrix as indicated at block 208 and allowing the fungal material to dry such that the water evaporates thereby creating a PLA coating on the fungal material with improved abrasion resistance and water resistance as indicated at block 210. Pressing the PLA coated fungal material at an elevated temperature to promote cross-linking which results in greater water-resistance and lower susceptibility to break-down in the presence of moisture as indicated at block 212.

The method further comprises adding at least one surfactant to the PLA coated fungal material 100 to improve the effectiveness of the abrasion resistant finish 102. The at least one surfactant may include at least one of polyurethane binder, isopropyl alcohol and 2-butoxyethanol. The addition of the at least one surfactant provides a polyurethane or acrylic containing layer to promote adhesion, followed by additional layers that contain color pigment, other acrylics, silicones or resins.

In one embodiment the method for creating an abrasion resistant finish comprises the steps of: providing an optimum quantity of a biodegradable polymer; dispersing the optimum quantity of the biodegradable polymer into water to produce a mixture; shaking the mixture to prevent the biodegradable polymer components from being separated or settled in water; applying the mixture onto the fungal material surface such that the water carries the biodegradable polymer deeply into the fungal matrix; allowing the fungal material to dry such that the water evaporates thereby creating a biodegradable polymer coating on the fungal material with improved abrasion resistance and water resistance; and pressing the biodegradable polymer coated fungal material at an elevated temperature to promote cross-linking that results in greater water-resistance and lower susceptibility to break-down in the presence of moisture.

In some embodiments the concentration of the biodegradable polymer dispersed in water can range from 0.1%-50.0%. In some embodiments the method further comprises adding at least one surfactant to the biodegradable polymer coated fungal material to improve the effectiveness of the abrasion resistant finish. In some embodiments the method further comprises at least one surfactant including a polyurethane binder, isopropyl alcohol and 2-butoxyethanol. In some embodiments the method includes the addition of the at least one surfactant provides a polyurethane or acrylic containing layer to promote adhesion, followed by additional layers that contain color pigment, other acrylics, silicones or resins. In some embodiments the mixture is applied in several coats and allowed to dry between 20° C. and 80° C. depending on desired finish qualities. In some embodiments the use of reduced local barometric pressure improves penetration and evaporation of the water component in the coating mixture. In some embodiments, the biodegradable polymer is a polyester, and in still further embodiments the polyester is a polylactic acid.

The penetration of the abrasion resistant finish 102 may be measured with methods including ISO 17186:2011 (Determination of Surface Coating Thickness), which specifies a method for determining the thickness of the surface coating applied to leather when measured under zero compression.

The adhesion of the abrasion resistant finish 102 may be measured with standard methods such as ISO 11644:2009 (Leather—Test for adhesion of finish), where adhesion is defined as the force required to pull the leather away from its surface finish layer, the force being applied steadily, at an angle of about 90°, to a rigid adherent-plate to which the finished side of the leather has been bonded with a minimally-penetrating adhesive.

In some embodiments the mycelium mass has a surface with a finish adhesion of at least 2 N/10 mm, while in other embodiments at least 3 N/10 mm. In some embodiments these measurements are according to ISO 11644:2009. In some embodiments the mycelium mass has a surface with a finish adhesion of at least 2 N/10 mm, while in other embodiments at least 3 N/10 mm. In some embodiments these measurements are according to ISO 11644:2009. In some embodiments the biodegradable mixture penetrates said surface to a depth of at least 20 micrometers, while in others at least 40 micrometers. In some embodiments these measurements are according to ISO 11644:2009. In still further embodiments the penetration is at least 1% but no more than 10%.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

What is claimed is:

1. An abrasion resistant finish obtained by following steps: producing a polylactic acid plastic (PLA) mixture by dispersing a biodegradable PLA in water, the PLA mixture carried by the water more deeply into the micro and macro structure of the fungal material, the PLA mixture penetrates into a matrix of a fungal hyphae of the fungal material and fortifies a hyphal structure as the water evaporates and creates a biodegradable PLA coating on the fungal material with improved abrasion resistance and water resistance, wherein the fungal material is mycelium; and at least one surfactant added to the biodegradable PLA coating on the fungal material to improve the effectiveness of the PLA coating, the surfactant further including isopropyl alcohol and a polyurethane binder.

2. The abrasion resistant finish of claim 1 wherein a quantity of the biodegradable PLA dispersed in water, depends on a thickness of the mixture coating to be applied on the fungal material and a surface density of the fungal material.

3. The abrasion resistant finish of claim 2 wherein the at least one surfactant further includes 2-butoxyethanol.

4. An abrasion resistant finish obtained by following steps: producing a polylactic acid (PLA) mixture by dispersing a biodegradable PLA in water, the water carries the PLA mixture more deeply into the micro and macro structure of the fungal material, the PLA mixture penetrates into a matrix of a fungal hyphae of the fungal material, wherein the fungal material is mycelium, and fortifies a hyphal structure as the water evaporates and creates a biodegradable PLA coating adhered on top of the fungal material with improved abrasion resistance and water resistance thereby providing strong adhesion between the PLA coating and the fungal material; and a surfactant added to the biodegradable PLA coating on the fungal material, the surfactant further including isopropyl alcohol and a polyurethane binder.

5. The abrasion resistant finish of claim 4 wherein a quantity of the biodegradable PLA is dispersed in water, which depends on a thickness of the mixture coating to be applied on the fungal material and a surface density of the fungal material.

6. The abrasion resistant finish of claim 4 wherein the at least one surfactant further includes 2 butoxyethanol.

* * * * *